US012350463B2

(12) United States Patent
Stephens et al.

(10) Patent No.: US 12,350,463 B2
(45) Date of Patent: *Jul. 8, 2025

(54) VALVE FOR DILATOR AND SHEATH ASSEMBLY

(71) Applicant: MEDICAL COMPONENTS, INC., Harleysville, PA (US)

(72) Inventors: John Stephens, Perkiomenville, PA (US); Kevin E. Sanford, Chalfont, PA (US); Jeffrey S. Bennett, Pottstown, PA (US); Burton W. Thomas, Broomall, PA (US); W. Shaun Wall, North Wales, PA (US); Christian K Peterson, Pottstown, PA (US)

(73) Assignee: MEDICAL COMPONENTS, INC., Harleysville, PA (US)

( * ) Notice: Subject to any disclaimer, the term of this patent is extended or adjusted under 35 U.S.C. 154(b) by 202 days.

This patent is subject to a terminal disclaimer.

(21) Appl. No.: 17/659,237

(22) Filed: Apr. 14, 2022

(65) Prior Publication Data
US 2022/0233838 A1    Jul. 28, 2022

Related U.S. Application Data

(63) Continuation of application No. 15/718,722, filed on Sep. 28, 2017, now Pat. No. 11,565,101, which is a
(Continued)

(51) Int. Cl.
*A61M 39/22* (2006.01)
*A61M 25/00* (2006.01)
(Continued)

(52) U.S. Cl.
CPC ........ *A61M 39/22* (2013.01); *A61M 25/0097* (2013.01); *A61M 25/0668* (2013.01);
(Continued)

(58) Field of Classification Search
CPC ............. A61M 39/22; A61M 39/0606; A61M 25/0097; A61M 29/00; A61M 25/0668;
(Continued)

(56) References Cited

U.S. PATENT DOCUMENTS

| 4,772,266 A | 9/1988 | Groshong |
| 5,006,113 A | 4/1991 | Fischer |
| (Continued) | | |

FOREIGN PATENT DOCUMENTS

| EP | 631793 A1 | 1/1995 |
| EP | 2179763 A1 | 4/2010 |
| (Continued) | | |

OTHER PUBLICATIONS

Search report dated Jan. 22, 2018, PCT/US2013/041109.
(Continued)

*Primary Examiner* — Bhisma Mehta
*Assistant Examiner* — Hamza A Darb
(74) *Attorney, Agent, or Firm* — John E. Boyd; FisherBroyles, LLP

(57) ABSTRACT

A valve for sealing the hub of a sheath assembly is provided. The valve includes a valve body having a solid thickness extending between a proximal surface and a distal surface. A bisecting slot extends across the proximal surface of the valve body and terminates at a depth less than the thickness of the valve body such that a portion of the valve body distally of the slot defines a bridge extending between opposed halves of the valve body such that the distal surface of the valve body is substantially continuous and a central portion of the proximal surface of the valve body is concave and defines a concave proximal portion.

20 Claims, 16 Drawing Sheets

Related U.S. Application Data continuation of application No. 13/832,294, filed on Mar. 15, 2013, now abandoned.

(60) Provisional application No. 61/725,509, filed on Nov. 13, 2012, provisional application No. 61/648,132, filed on May 17, 2012.

(51) Int. Cl.
*A61M 25/06* (2006.01)
*A61M 29/00* (2006.01)
*A61M 39/06* (2006.01)

(52) U.S. Cl.
CPC ........ *A61M 29/00* (2013.01); *A61M 39/0606* (2013.01); *A61M 2025/0681* (2013.01); *A61M 2039/064* (2013.01); *A61M 2039/066* (2013.01)

(58) Field of Classification Search
CPC ...... A61M 2039/066; A61M 2039/064; A61M 2025/0681; A61M 39/06; B29C 66/71; A61B 17/3498

See application file for complete search history.

(56) References Cited

U.S. PATENT DOCUMENTS

| | | | |
|---|---|---|---|
| 5,098,392 A | | 3/1992 | Fleischhacker et al. |
| 5,167,637 A | * | 12/1992 | Okada ............... A61M 39/0606 |
| | | | 604/167.04 |
| 5,199,948 A | | 4/1993 | McPhee |
| 5,273,546 A | | 12/1993 | McLaughlin et al. |
| 5,885,217 A | | 3/1999 | Gisselberg et al. |
| 6,796,991 B2 | | 9/2004 | Nardeo |
| 6,951,295 B1 | | 10/2005 | Gaus et al. |
| 7,422,571 B2 | | 9/2008 | Schweikert et al. |
| 7,637,893 B2 | | 12/2009 | Christensen et al. |
| 7,972,307 B2 | * | 7/2011 | Kraus ............... A61M 25/0662 |
| | | | 604/167.03 |
| 8,753,317 B2 | | 6/2014 | Osborne et al. |
| 11,565,101 B2 | * | 1/2023 | Stephens ............... A61M 29/00 |
| 2004/0267202 A1 | | 12/2004 | Potter |
| 2005/0010238 A1 | | 1/2005 | Potter et al. |
| 2005/0192537 A1 | | 9/2005 | Osborne et al. |
| 2006/0030817 A1 | | 2/2006 | Kraus et al. |
| 2009/0143739 A1 | * | 6/2009 | Nardeo ............. A61M 39/0693 |
| | | | 604/167.04 |
| 2010/0100044 A1 | | 4/2010 | Ye et al. |
| 2010/0101069 A1 | * | 4/2010 | Christensen ...... A61M 39/0693 |
| | | | 29/428 |
| 2010/0179480 A1 | | 7/2010 | Sugiki et al. |
| 2010/0241083 A1 | * | 9/2010 | Fisher ............... A61M 25/0097 |
| | | | 604/167.04 |
| 2013/0072956 A1 | | 3/2013 | Searfoss et al. |

FOREIGN PATENT DOCUMENTS

| | | |
|---|---|---|
| JP | 3941022 B2 | 5/1999 |
| JP | 11128359 | 5/1999 |
| WO | 2009002828 A2 | 12/2008 |
| WO | 2009038727 A1 | 3/2009 |

OTHER PUBLICATIONS

Canadian Office Action, issued by the Canadian Intellectual Property Office, regarding corresponding patent application Serial No. CA 2873988; dated Jan. 22, 2018, 4 pages.

International Search Report and Written Opinion, issued by the ISA/European Patent Office, regarding corresponding International patent application Serial No. PCT/US2013/041109, dated Aug. 26, 2013; 15 pages.

\* cited by examiner

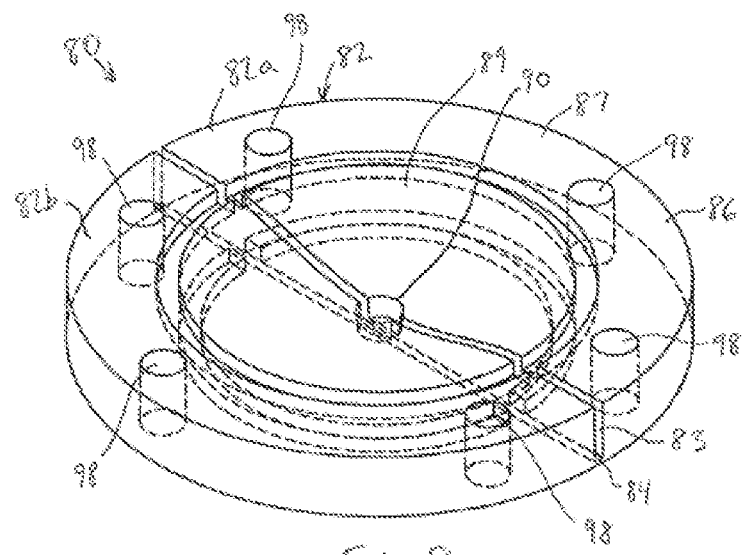

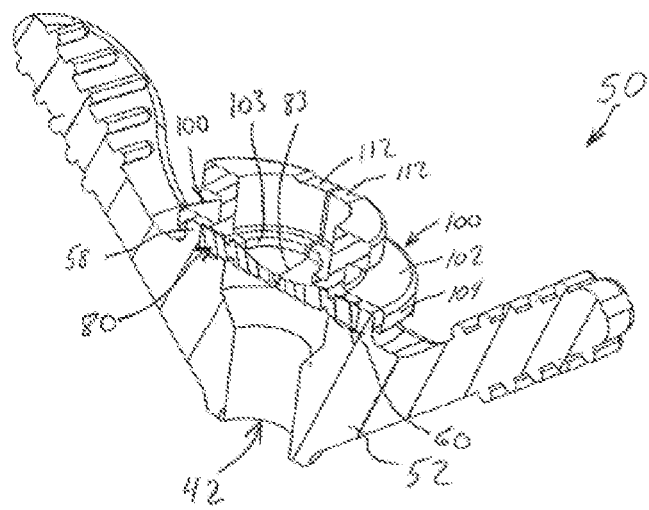

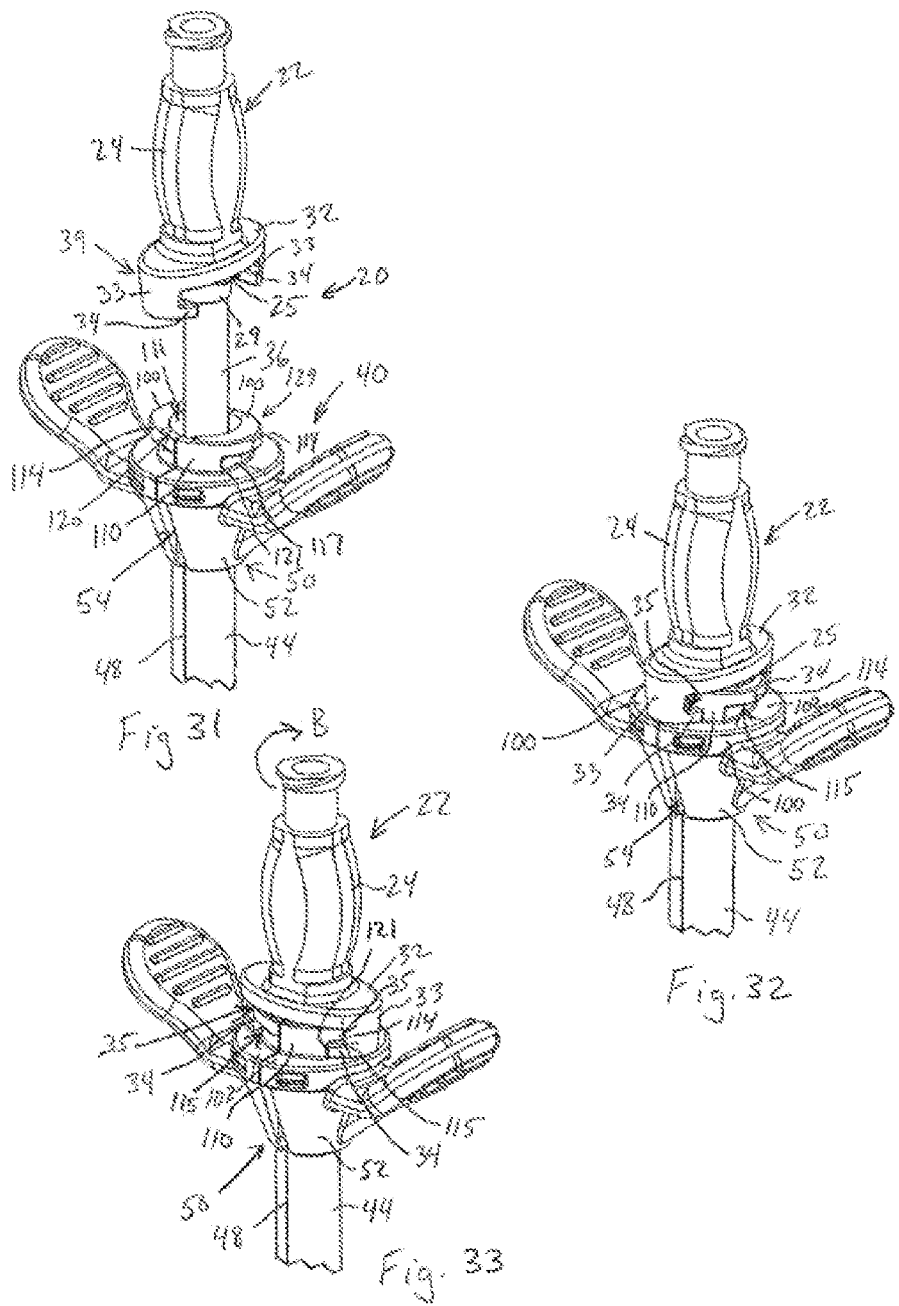

VALVE FOR DILATOR AND SHEATH ASSEMBLY

CROSS REFERENCE TO RELATED APPLICATIONS

This application is a continuation of U.S. patent application Ser. No. 15/718,722 filed Sep. 28, 2017, which issued as U.S. Pat. No. 11,565,101 on Jan. 31, 2023; which is a continuation of U.S. patent application Ser. No. 13/832,294, filed Mar. 15, 2013; which claims the benefit of U.S. Provisional application Ser. No. 61/725,509, filed on Nov. 13, 2012; and which claims the benefit of U.S. Provisional application Ser. No. 61/648,132, filed on May 17, 2012; the entireties of which are incorporated herein by reference.

FIELD OF THE INVENTION

This invention relates to invasive medical devices which aid in the catheterization of human blood vessels. In particular, this invention relates to a releasably locking dilator and tear away sheath assembly, which is used to enlarge an opening in a patient's blood vessel during insertion of a catheter into the blood vessel and then guide the catheter into the blood vessel to be catheterized.

BACKGROUND OF THE INVENTION

Catheters are used in numerous medical procedures. In particular, catheters are used for the introduction or removal of fluids from various venous regions and vessels throughout the body, such as for hemodialysis. The procedure by which these catheters are introduced to the body is delicate and complex. One particularly intricate challenge to catheterization is enlarging a hole in the flesh and vessel to be cathetrized while minimizing blood loss and trauma to the patient.

Generally, to insert any catheter in a blood vessel, the vessel is identified by aspiration with a long hollow needle in accordance with the Seldinger technique. When blood enters a syringe attached to the needle, indicating that the vessel has been found, a thin guide wire is then introduced, typically through the syringe needle or other introducer device, into the interior of the vessel. The introducer device is then removed, leaving the guide wire within the vessel. The guide wire projects beyond the surface of the skin.

At this point, several options are available to a physician for catheter placement. The simplest option is to pass a catheter into the vessel directly over the guide wire. The guide wire is then removed. However, use of this technique is only possible in cases where the catheter is of a relatively small diameter, made of a stiff material and not significantly larger than the guide wire. If, however, the catheter is of a relatively large diameter and/or made of a soft material, one preferable method of inserting the catheter into the vessel is through an introducer sheath. The introducer sheath is simply a large, stiff, thin-walled tube, which serves as a temporary conduit for the catheter that is being placed. The sheath is positioned by placing a dilator, which has a hollow passageway along its longitudinal axis, inside of the sheath and passing both the dilator and the sheath together into the vessel over the guide wire. The dilator expands the opening in the blood vessel to allow for catheter insertion into the vessel. The guide wire and dilator are then removed, leaving the thin-walled sheath in place. The catheter is then inserted into the vessel through the sheath.

In a setting where a catheter with a hub or other attachment at the proximal end of the catheter has a feature which is larger than that of the inner diameter of the sheath, it is necessary to have a tear-away sheath that can be split away from the catheter as the sheath is being removed from the patient. By splitting the sheath along its longitudinal axis as the sheath is being removed from the patient, the inserting physician will be able to pull out the sheath in such a way that the portion removed from the patient is split, thereby not interfering with any encumbrances on the catheter. Generally, tear away sheaths are manufactured in a way that aids in the tearing of the sheath at two opposing points on the circumference of the sheath, thereby splitting the sheath into two halves separated longitudinally through the center of the sheath.

A sheath is generally constructed with a hub at its proximal end. This hub serves as a handle, a mating point for a dilator, and a flat surface to aid in the prevention of blood loss or contamination. When a sheath needs to be split apart in order to be successfully withdrawn from the body while leaving the catheter in place, the hub will also have to be split apart in order to clear the catheter. Preferably, the hub will split along the same lines as the sheath. To accomplish this, the hub must be designed with reveals or other weaknesses along two longitudinal lines aligned with the weaknesses in the sheath. Some previous examples of these weaknesses are tabs or webs which connect two halves of the hub, or recesses in the material comprising the hub. The weaknesses in the hub will help the inserting physician to break apart the hub in line with the tear seams on the sheath.

Another important facet of the hub is a set of tabs that protrude from the center. These tabs not only help the inserting physician to align, insert and withdraw the sheath, but also to pull the sheath so that the sheath can be removed from around a catheter while still leaving the catheter in place. There are a number of different tab configurations, but it is important to have one which allows for easy maneuverability, control, and leverage. One design includes a hub wherein the tabs protrude from the hub perpendicular to a plane which includes the tear seams in the sheath and the longitudinal axis of the sheath. In this design, the tabs are diametrically opposed from each other and are spaced in such a way that when the tabs are grasped and pulled apart from each other, the sheath and its hub will split down the middle. Another desirable feature of the tabs is that the tabs provide leverage for breaking apart the hub in a manner that does not cause trauma to the incision in the body.

During insertion, especially in the time between the removal of the dilator from the sheath and the insertion of the catheter through the sheath, it is possible for blood loss through the sheath, or the introduction of contaminants or air through the sheath and into the vessel. For this reason, it is desirable that measures be taken to prevent blood, air or contaminants from traveling through the sheath. In the past, inserting physicians have simply held their thumb over the opening in the proximal end of the sheath; however, a more permanent and reliable means for preventing blood, air or contaminants from traveling through the sheath is desirable. It is therefore desirable for the hub to include a valve located in the sheath. Such a valve would facilitate the insertion of objects such as a catheter or dilator through the sheath while restricting blood loss and reducing the chance of contaminants entering the patient's bloodstream when the sheath is not engaged with a dilator or a catheter.

The dilator has a long tubular section, the outside diameter of which is slightly smaller than the inside diameter of the sheath. The dilator also has a pointed tip on its distal end and a hollow center, which runs along the entire length of the dilator. The dilator is inserted into the body with the guidewire running through its center, thereby allowing the tip of the dilator to follow the guidewire to the place that is to be catheterized. On its proximal end, the dilator may have a hub. Like the hub of the sheath, this hub can also serve a number of purposes, such as providing a stable handle to aid in guiding the dilator into the vein, and as a mechanism which can mate with the sheath hub to form a locked connection.

Some dilator and sheath assemblies that include a connection between the dilator and sheath are known. U.S. Pat. No. 5,885,217 to Gisselberg et al. discloses a dilator and sheath assembly, wherein the dilator and sheath are held together by locking tabs which provide a stop to hold the dilator in place during insertion. However, in this configuration, the dilator may rotate about its longitudinal axis in relation to the sheath, thereby inadvertently and prematurely disengaging the dilator from the sheath. U.S. Pat. No. 5,098,392 to Fleischhacker et al. discloses a dilator and sheath assembly, wherein the dilator is attached to the sheath through a clamp wherein the clamp is part of the dilator hub. However, this design presents the ability to come unclamped leading to the dilator backing out of the sheath. U.S. Pat. No. 4,772,266 to Groshong discloses a dilator and sheath assembly, wherein the hubs of the dilator and the sheath lock together by means of compression. However, it would be possible for the dilator to back out of the sheath in this configuration if excessive force is exerted on the tip of the dilator.

It would be beneficial to provide a dilator and sheath assembly that incorporates a stable releasably locking mechanism to prevent the dilator from backing out of the sheath longitudinally during insertion which is not prone to coming unlocked or releasing during use. It would also be beneficial for the sheath of the dilator and sheath assembly to have a means for sealing the passageway to the patient's vessel, thereby restricting blood loss and reducing the introduction of contaminants into the bloodstream.

SUMMARY OF THE INVENTION

Briefly, the present invention provides a releasably locking dilator and sheath assembly and methods for releasing the dilator from the sheath and longitudinally splitting the sheath in the course of inserting a catheter into a desired vessel to be catheterized.

In one aspect, the invention provides a valve for sealing the hub of a sheath assembly, the valve comprising a valve body with a bisecting slot extending into a proximal surface of the valve body and terminating at a depth less than the thickness of the valve body such that the remaining portion of the valve body distally of the slot defines a bridge extending between opposed halves of the valve body such that a distal surface of the valve body is substantially continuous.

In another aspect, the invention provides a sheath assembly including an elongated hollow sheath body having a proximal body end, a distal body end, and a longitudinal axis extending between the proximal body end and the distal body end. A sheath hub is fixedly connected to the proximal body end and includes a hub proximal end and a hub distal end with a through passage extending from the hub distal end to the hub proximal end and in communication with the hollow sheath body. The sheath hub further defining a valve seat proximate the hub proximal end. A valve is seated in the valve seat and includes a valve body with a bisecting slot extending into a proximal surface of the valve body and terminating at a depth less than the thickness of the valve body such that the remaining portion of the valve body distally of the slot defines a bridge extending between opposed halves of the valve body such that a distal surface of the valve body is substantially continuous, the valve extending across and sealing the through passage.

In a further aspect, the sheath body of the sheath assembly includes at least one tear seam extending in a plane between the proximal body end and the distal body end and the sheath hub includes at least one longitudinal notch, and the at least one tear seam, the at least one longitudinal notch and the bisecting slot are co-planar.

In another aspect, the invention provides a dilator and sheath assembly. The dilator includes an elongated dilator stem having a proximal dilator end and a dilator hub fixedly connected to the proximal dilator end, wherein the dilator hub includes a locking portion at a distal portion thereof. The sheath assembly includes an elongated tubular portion having a proximal sheath end, a distal sheath end, and a longitudinal axis extending between the proximal sheath end and the distal sheath end, wherein the tubular portion is sized to receive the dilator stem and includes at least one tear seam extending in a plane between the proximal sheath end and the distal sheath end. A sheath hub is fixedly connected to the proximal sheath end. A valve is assembled to the sheath hub proximal of the proximal sheath end and at least one cap member is secured to the sheath hub proximal portion. The at least one cap member defines a mating locking portion wherein the locking portion of the dilator hub and the mating locking portion of the cap provide a releasably locking engagement between the dilator and the sheath.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 8 is a top perspective view of an exemplary valve in accordance with an embodiment of the invention.

FIG. 9 is a bottom perspective view of the exemplary valve of FIG. 8.

FIG. 28 is a perspective cross-sectional view along the line 28-28 in FIG. 27.

FIG. 29 is a planar view of the cross-sectional view of FIG. 28.

FIGS. 31-33 are perspective views of the releasably locking dilator and the sheath assembly sequentially illustrating positioning and locking of the dilator relative to the sheath assembly.

DETAILED DESCRIPTION OF THE INVENTION

Figure 1:
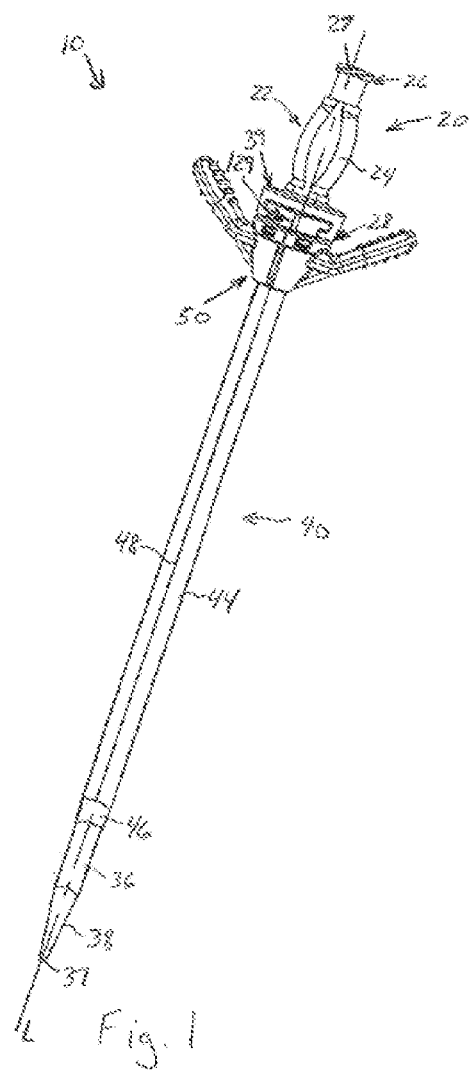
FIG. 1 is a perspective view of a releasably locking dilator and sheath assembly in a locked state in accordance with an embodiment of the present invention.

In the drawings, like numerals indicate like elements throughout. Certain terminology is used herein for convenience only and is not to be taken as a limitation on the present invention. The terms "distal" and "proximal" refer to the directions "away from" and "closer to," respectively, the body of the physician inserting the dilator and sheath assembly into a patient. As used herein, the term "slot" refers to a separation of material of a body which extends only partially through the body and does not exit out an opposite surface of the body and the term "slit" refers to a separation of material of a body which passes through the body from one surface out the other surface. The terminology includes the words above specifically mentioned, derivatives thereof, and words of similar import. The following describes a preferred embodiment of the present invention. However, it should be understood, based on this disclosure, that the invention is not limited by the preferred embodiment described herein.

Figure 2:
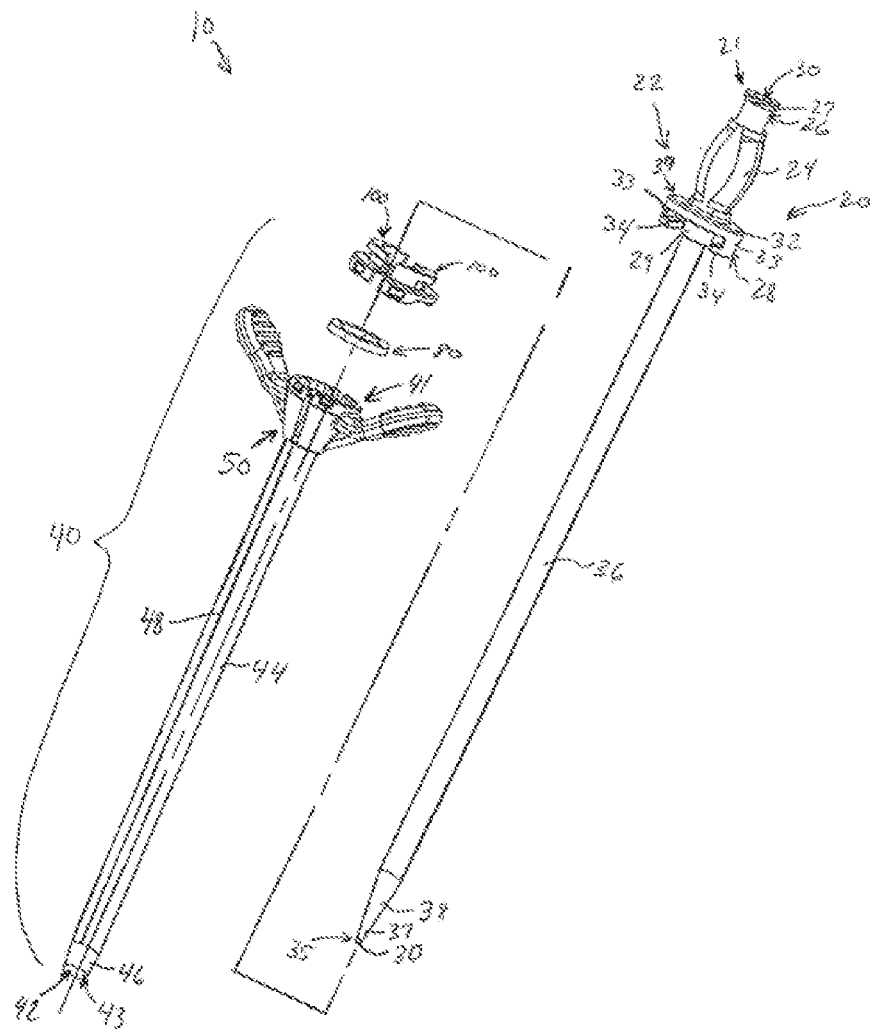
FIG. 2 is an exploded perspective view of the assembly of FIG. 1.
Figure 3:
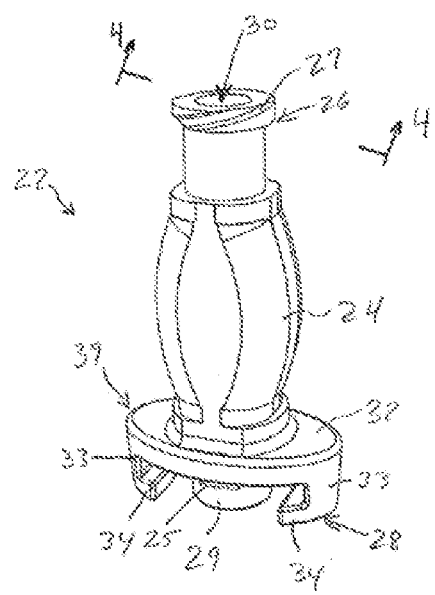
FIG. 3 is a perspective view of an exemplary dilator hub in accordance with an embodiment of the invention.
Figure 4:
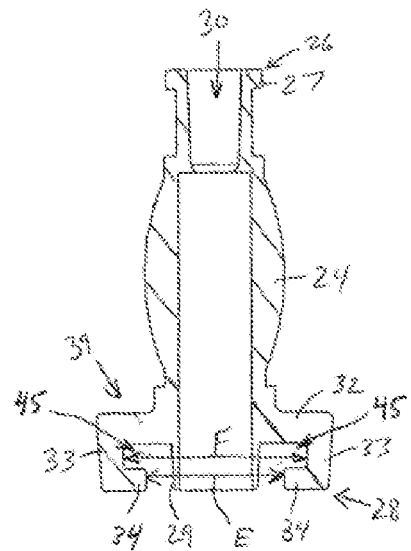
FIG. 4 is a cross-sectional view along the line 4-4 in FIG. 3.

Referring to FIGS. 1 and 2, an exemplary embodiment of a releasably locking dilator and sheath assembly 10 is shown. The assembly 10 generally includes a dilator 20 and a sheath assembly 40, which are releasably lockable to each other. The dilator 20 is longer than the sheath assembly 40 so that the dilator 20, in the releasably locked position as shown in FIG. 1, passes through the sheath assembly 40 so that a distal tip 37 of the dilator 20 extends beyond the distal end 46 of the sheath assembly 40.

Referring to FIGS. 1-4, the dilator 20 is an elongated device that includes a proximal end 21, a distal end 35 with a stem 36 and dilator hub 22 extending between the proximal end 21 and the distal end 35. At the distal end 35 of the dilator stem 36, a transition portion 38 reduces in diameter to a conically shaped, open distal tip 37. When in a releasably connected state with the dilator 20 inside of the sheath assembly 40, the dilator 20 and sheath assembly 40 share the same longitudinal axis "L". The exterior diameter of the stem 36 of the dilator 20 is sized to allow a slight frictional engagement between the inside of the distal end 46 of the sheath body 44 and the outside of the dilator stem 36. This frictional engagement serves to form a seal between the dilator 20 and the sheath assembly 40 and reduce or prevent blood seepage through the sheath assembly 40 while the dilator 20 is releasably connected thereto. Preferably, the dilator 20 includes a hollow passageway 30 along the length of the dilator 20 from the distal tip 37 to the proximal end of the dilator hub 22. The hollow passageway 30 allows the dilator 20 to be inserted over a guidewire (not shown) and follow the guidewire to the desired position inside the vessel to be catheterized.

The proximal end 21 of the dilator 20 comprises a dilator hub 22 fixedly connected to the dilator stem 36 such as by an adhesive, ultrasonic bonding, insert molding or another method known to those skilled in the art. The dilator hub 22 includes a body 24 extending between a proximal end 26 and a distal end 28. The proximal end 26 includes a connector 27, for example, the male portion of a luer connector. The connector 27 may be used as a temporary fitting for any apparatus (not shown) that may be required to be attached to the dilator 20. The distal end 28 of the dilator hub 22 includes a connector ring 29 configured to receive a proximal end of the stem 36 whereat the stem 36 is fixedly connected to the hub 22. Alternatively, the ring 29 may be received within the stem 36 and fixedly connected.

A locking portion 39 extends from the hub body 24 adjacent to the distal end 28 of the hub 22. The locking portion 39 of the present embodiment includes an elongate platform 32 extending radially from the hub body 24. The platform 32 preferably has a length larger than its width such that the platform 32 extends from opposed sides of the hub body 24. An extension portion 33 extends from each end of the platform 32, extending substantially parallel to the axis L. An engagement portion 34 extends perpendicularly from each extension portion 33 substantially parallel to the platform 32 such that locking grooves 45 are defined on opposite sides of the hub body 24. The inside surfaces of the extension portions 33 are spaced from one another a distance F while the engagement portions 34 are spaced from one another by a distance E. Preferably, a stop member 25 depends from each side edge of the platform 32. The locking portion 39 is configured to engage a portion of the sheath assembly 40 to lock the dilator 20 relative thereto, as will be described in more detail hereinafter.

Referring to FIGS. 1 and 2, the sheath assembly 40 is used to aid in the insertion of a catheter (not shown) into a vessel (not shown) to be catheterized, as is well known in the art. Since the sheath assembly 40 includes a sheath body 44 which is generally more rigid than a catheter, the sheath assembly 40 can be maneuvered into place with less effort and trauma to the patient than a catheter. The catheter is then inserted into the vessel through the sheath assembly 40.

Once the catheter is in place, the sheath assembly 40 may be removed, thereby leaving the catheter in its desired position. If the sheath assembly 40 has any encumbrance, such as a hub, on its proximal end, the sheath assembly 40 will have to be split in order to remove it from the patient's body while leaving the catheter in place.

In the present embodiment, the sheath assembly 40 extends between a proximal end 41 and a distal end 43 and includes a sheath body 44, a sheath hub 50, a valve 80 and cap members 100. A through passage 42 extends through the sheath body 44 and sheath hub 50 from the distal end 43 to the proximal end 41. The through passage 42 is sealed by the valve 80 as described in more detail hereinafter.

The sheath body 44 is a hollow tubular member which preferably has a tapered distal end 46. At least one tear seam 48 is longitudinally disposed along the entire length of the sheath body 44. In this preferred embodiment, two tear seams 48 are present. The tear seams 48 are located on opposite sides of the sheath body 44 such that a plane extending through the two tear seams 48 bisects the sheath body 44 longitudinally. Preferably, the plane contains the longitudinal axis L. The proximal end of the sheath body 44 is fixedly connected to the distal end of the sheath hub 50.

Figure 5:
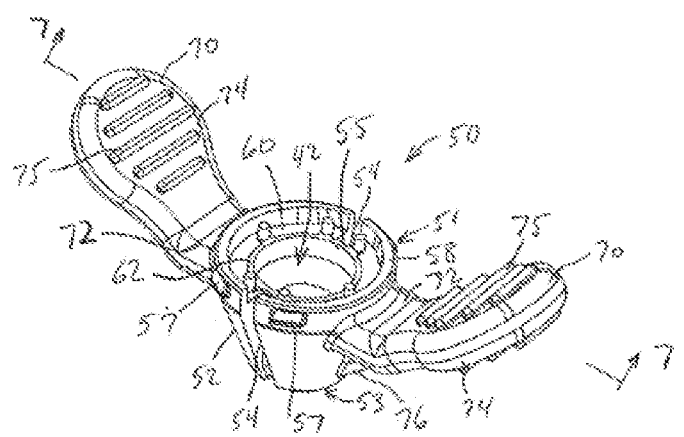
FIG. 5 is a top perspective view of an exemplary sheath hub in accordance with an embodiment of the invention.
Figure 6:
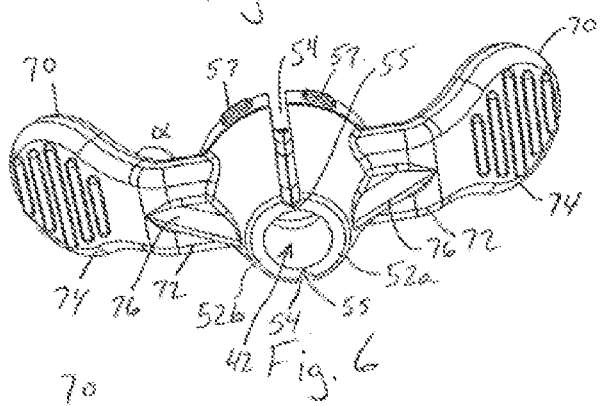
FIG. 6 is a bottom perspective view of the exemplary sheath hub of FIG. 5.
Figure 7:
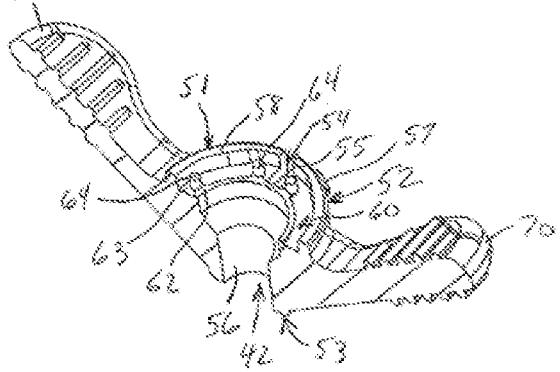
FIG. 7 is a cross-sectional view along the line 7-7 in FIG. 5.

Referring to FIGS. 5-7, the sheath hub 50 includes a conical body 52 which tapers from a wider proximal end 51 to a narrower distal end 53. Two diametrically opposed notches 54 are defined longitudinally along the hub body 52 from the distal end 53 to the proximal end 51. At the radial inner end of each notch 54, a bridge 55 extends between the two opposed halves 52a, 52b of the body 52. The hub body 52 is preferably molded as a unitary component with the bridges 55 extending between the halves 52a, 52b and the notches 54 preformed, however, the hub body 52 may be otherwise formed. For example, the body halves 52a, 52b may be formed as separate components which are joined by the bridges 55 after formation. Alternatively, the body 52 may be formed as a unitary structure without any notches and the notches are formed through a post molding process, leaving just the bridges 55 extending between the halves 52a, 52b. While continuous bridges 55 are illustrated, the invention is not limited to such and other structures, including those described in U.S. Pat. Nos. 6,796,991, 7,422,571 and 8,052,646, each of which is incorporated herein by reference, may be utilized to join the opposed halves 52a, 52b with a weakened tear line defined therebetween. Each notch 54 is preferably aligned with one of the tear seams 48 of the sheath body 44 such that the notches 54 and the tear seams 48 of the sheath body 44 are coplanar.

Referring to FIG. 7, the interior surface of the hub body 52 at the distal end defines a conical surface 56 configured to receive and fixedly connect the sheath body 44 proximal end. The sheath hub 50 is fixedly connected to the proximal end of the sheath body 44 such as by an adhesive, ultrasonic bonding, insert molding or any other method known to those skilled in the art. The diameter of this conical surface 56 may be manufactured to different sizes to allow the hub 50 to be used with larger or smaller size sheath bodies 44. Alternatively, the conical surface 56 may be manufactured to a standard size and a spacer ring (not shown) may be positioned between the sheath body 44 and the conical surface 56 to sealingly close the distal end of the hub body 52.

The interior surface of the hub body 52 tapers outwardly from the conical surface 56 to an annular valve seat 60 which extends about the through passage 42. The proximal end 51 of the hub body 52 defines an annular wall 58 about the valve seat 60. The valve seat 60 includes a planar surface 62 extending about the through passage 42. The planar surface 62 is preferably continuous about the entire circumference of the through passage 42 such that it defines a continuous sealing surface. An annular groove 63 is defined between the planar surface 62 and the annular wall 58. A plurality of alignment posts 64 extend proximally from within the groove 63 and are configured properly align the valve 80 received within the valve seat 60 as described in more detail below.

A plurality of retaining tabs 57 extend radially outward from the outer surface of the wall 58 for securing the cap members 100 as described below. Each retaining tab 57 preferably tapers outwardly moving from the proximal end to the distal end.

First and second diametrically opposed winged tabs 70 extend from the sheath hub body 52 adjacent its proximal end 51. The tabs 70 are circumferentially offset 90.degree. relative to the notches 54. In the illustrated embodiment, the first and second tabs 70 each include a perpendicular portion 72, perpendicular to the longitudinal axis L and an angled portion 74. A brace member 76 may extend between each perpendicular portion 72 and a distal portion of the hub body 52. In addition to supporting the perpendicular portions 72, the braces 76 also help to concentrate the forces as the sheath hub 50 is torn away in a known manner. As shown in FIG. 6, an angle .alpha. extends between the proximal surface of the perpendicular portion 72 and the angled portion 74 of each of the winged tabs 42. The angle .alpha. ranges from approximately 90.degree. to approximately 179.degree. Preferably, the angle .alpha. is between approximately 130.degree. to approximately 140.degree.; however, those skilled in the art will recognize that the angle .alpha. can have other ranges as well. The angled portions 74 of the winged tabs 70 include raised ridges 75 on their proximal and distal surfaces to aid in gripping the tabs 70. Alternatively, other raised features on the winged tabs 70, such as bumps or a crosshatched pattern (not shown) may also assist the gripping the winged tabs 70.

The sheath body 44 is preferably constructed of high-density polyethylene, low-density polyethylene or polytetrafluoroethylene. The sheath hub 50 is preferably constructed of high-density polyethylene or polypropylene. The dilator stem 26 is preferably constructed of high-density polyethylene, low-density polyethylene or polypropylene. The dilator hub 22 is preferably constructed of high-density polyethylene or polypropylene.

Referring to FIGS. 8-12, an exemplary valve 80 will be described. The valve 80 has a cylindrical body 82 with a diameter substantially equal to or slightly larger than the inside diameter of the hub body annular wall 58. While the valve body 82 is shown as cylindrical, it may have any other shape which complements the shape of the valve seat 60 and annular wall 58. The body 82 extends between a proximal surface 86 and a distal surface 94. A bisecting slot 83 extends into the proximal surface 86 across the body 82 through the center thereof such that the body 82 includes opposed body halves 82a and 82b. The slot 83 terminates prior to the distal surface 94 such that the body halves 82a and 82b are joined by a bridging portion 84 along the distal surface 94. The bridging portion 84 has a reduced thickness t relative to the total thickness T of the valve body 82. Preferably, the thickness t of the bridging portion is between approximately 0.002 to 0.006 inches and more preferably between approximately 0.003 to 0.004 inches. For relative comparison, the valve body thickness may be about 0.1 inches. With this configuration, the bridging portion 84 retains the body halves 82a, 82b together prior to assembly and acts to seal the through passage 42, but remains easily split as an instrument is passed through the valve 80 and easily separated when the sheath assembly 40 is split.

The valve body 82 is preferably molded as a unitary component with the bridge portion 84 extending between the halves 82a, 82b and the slot 83 preformed, however, the valve body 82 may be otherwise formed. For example, the body halves 82a, 82b may be formed as separate components which are joined by the bridge portion 84 after formation. Alternatively, the body 82 may be formed as a unitary structure and the slot is formed through a post molding process, for example, cutting, leaving just the bridge portion 84 extending between the halves 82a, 82b. Preferably, the valve 80 is constructed of silicone, however, those skilled in the art will recognize that the valve 80 may be constructed out of any material that is sufficiently resilient to accommodate the objects inserted therethrough and return to a closed position. The material preferably has a durometer between 10 A to 40 A. The width G of the slot 83 is preferably minimal and is generally dictated by the method of manufacture. In the present embodiment, the width G is preferably about 0.005 inches, however, the width G may approach zero, as in simple separation of material, or may be larger than 0.005 inches. For example, if the slot 83 is formed through a post molding cutting operation, the width G may approach zero. Alternatively, the halves 82a, 82b may be molded at an angle to one another with the bridge portion 84 extending therebetween and the width G relatively large. As the halves 82a, 82b are pivoted toward one another into a common plane, the width G may approach zero.

Figure 30:
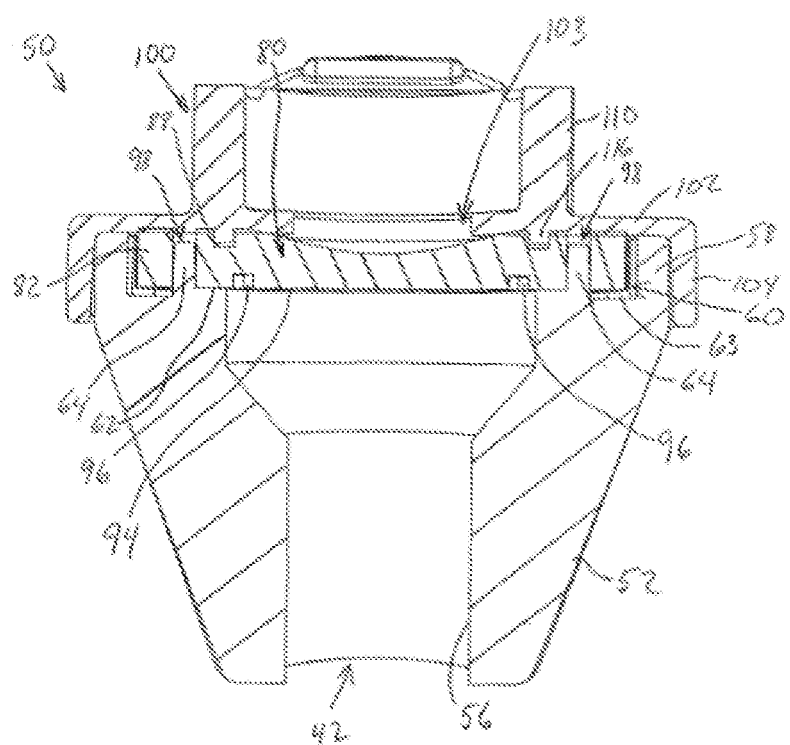
FIG. 30 is a cross-sectional view along the line 30-30 in FIG. 27.

The proximal surface 86 defines an outer annular planar portion 87 that is substantially perpendicular to the longitudinal axis L when the valve is assembled within the sheath hub 50 (see FIGS. 29 and 30). An annular groove 88 is defined along the planar portion 87 and is configured to receive a retaining ridge 116 of the cap members 100 and also facilitates hinging of a center portion of the valve body 82 as an item is passed through the valve 80, as described in more detail below. A plurality of alignment holes 98 extend from the distal surface 94 to the proximal surface 86 are defined circumferentially spaced about the planar portion 87. While the alignment holes 98 are illustrated extending completely through the body 82, such is not required. Alternatively, the alignment holes 98 may be formed as blind holes opening at the distal surface 94.

Figure 10:
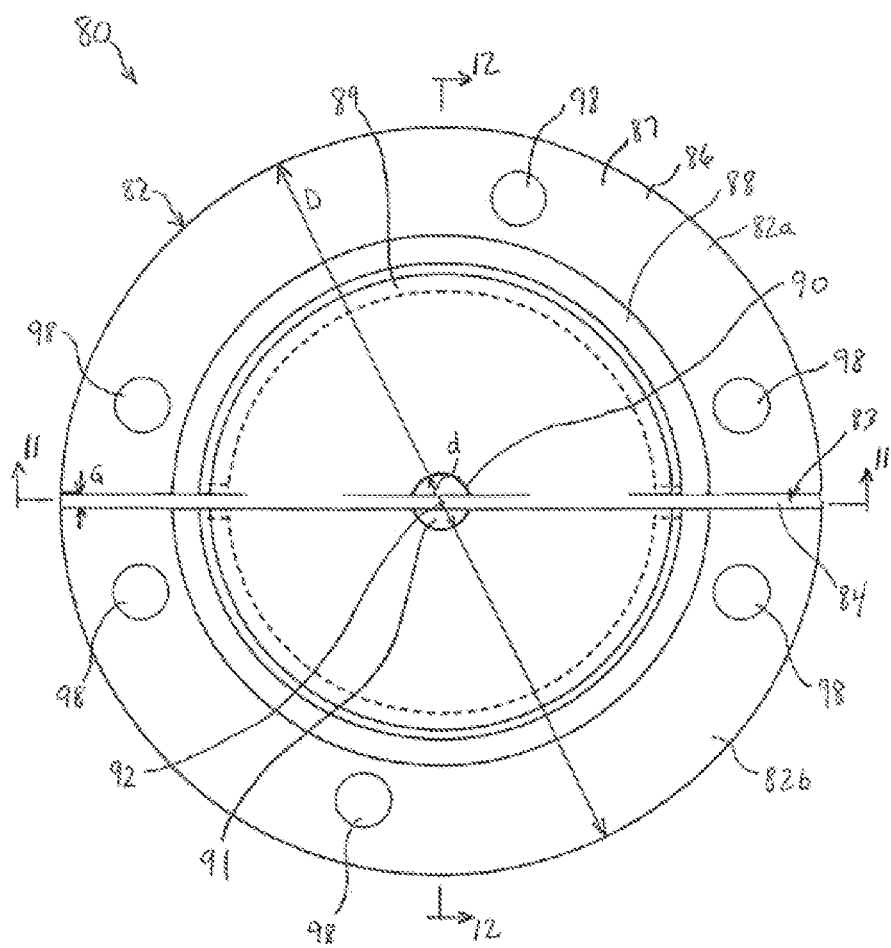
FIG. 10 is a top plan view of the exemplary valve of FIG. 8.
Figure 11:
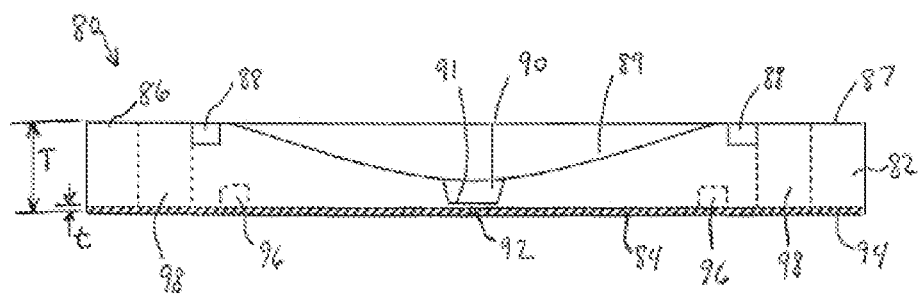
FIG. 11 is a cross-sectional view along the line 11-11 in FIG. 10.

The alignment holes 98 are configured to receive respective ones of the alignment posts 64 of the valve seat 60. As seen in FIG. 10, the alignment holes 98 are positioned in a non-symmetrical configuration. The alignment posts 64 are arranged in a corresponding configuration. As such, the valve 80 can only be positioned in the sheath hub 50 in a proper orientation with the proximal surface 86 facing proximally and the slot 83 co-planar with the notches 54.

Figure 12:
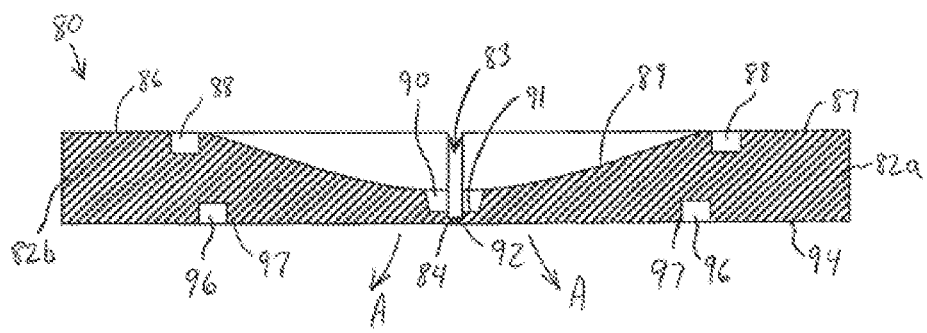
FIG. 12 is a cross-sectional view along the line 12-12 in FIG. 10.
Figure 13:
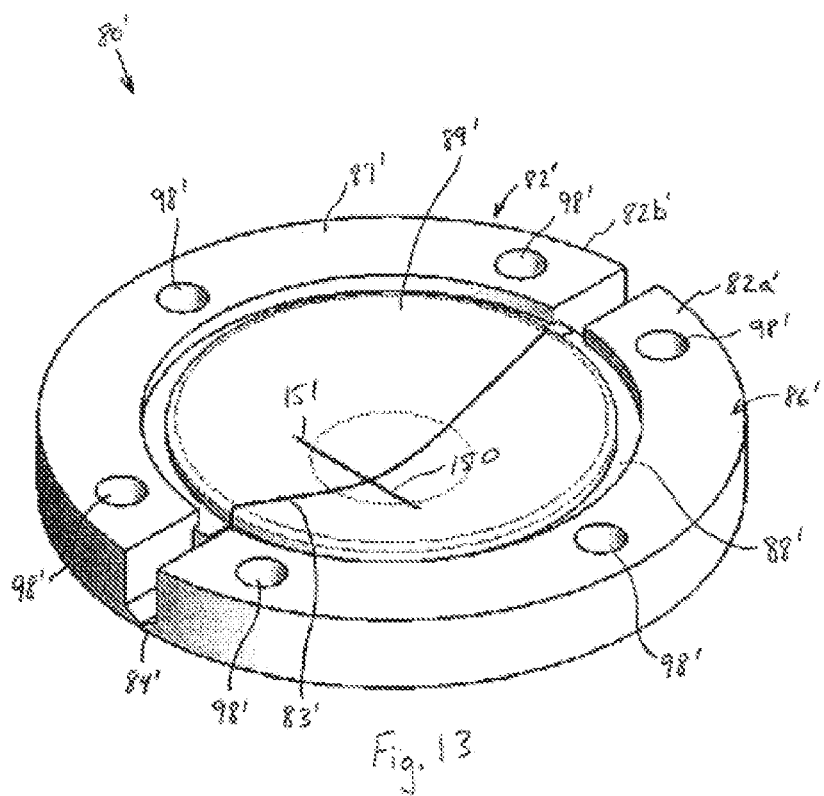
FIG. 13 is a perspective view of another exemplary valve in accordance with an embodiment of the invention.
Figure 14:
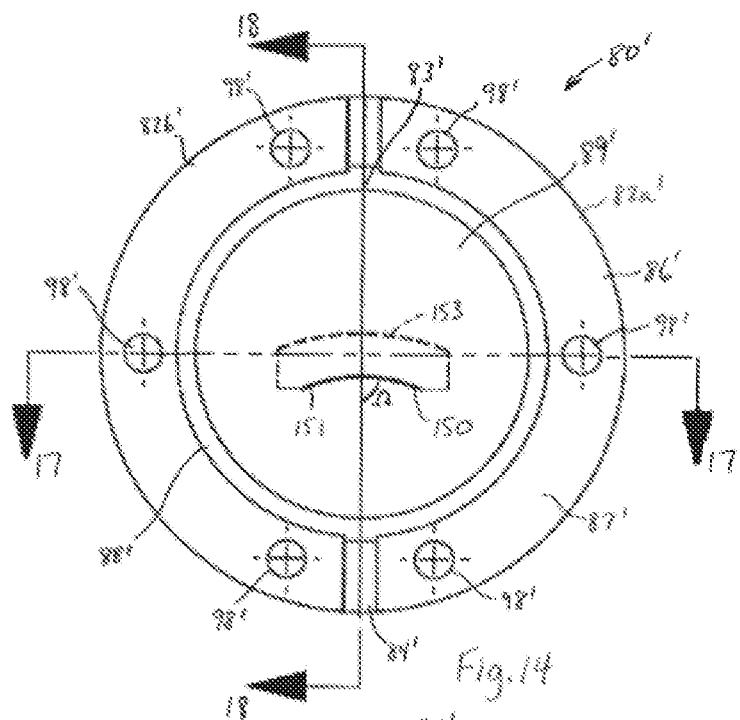
FIG. 14 is a top perspective view of the exemplary valve of FIG. 13.
Figure 15:
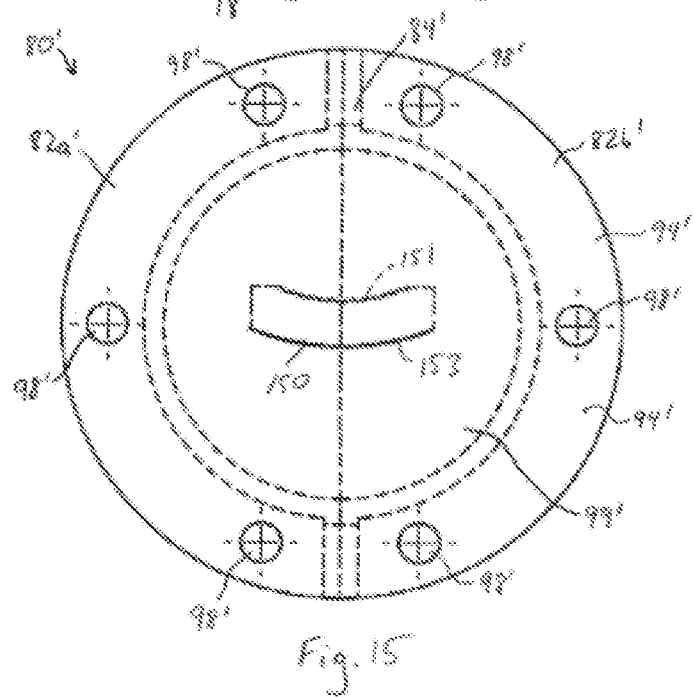
FIG. 15 is a bottom perspective view of the exemplary valve of FIG. 13.
Figure 16:
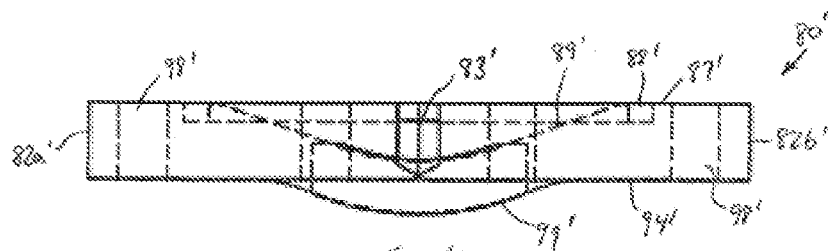
FIG. 16 is a side elevation view of the exemplary valve of FIG. 13.
Figure 17:
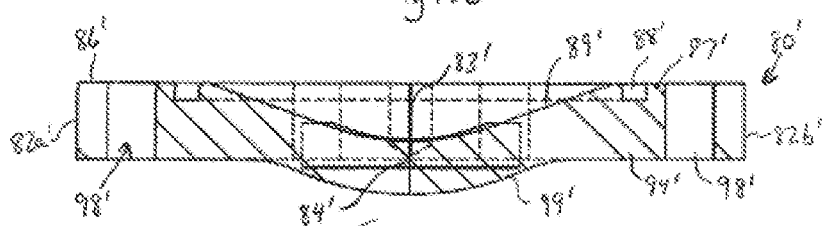
FIG. 17 is a cross-sectional view along the line 17-17 in FIG. 13.

Radially inward of the planar portion 87, the proximal surface 86 defines a conical portion 89 which tapers to a central blind bore 90. The bore 90 terminates in a bottom surface 91 that is spaced from the body distal surface 94 such that the bore 90 does not pass completely through the valve body 82. The bore 90 may be formed with a narrowing taper from the entrance at the conical portion 89 to the bottom surface 91. The conical portion 89 and the bore 90 serve to guide a guidewire (not shown), the dilator distal tip 37, the catheter tip (not shown), or any other instrument as they are respectively passed through the valve 80. The bore 90 has a diameter d which is relatively small compared to the diameter D of the valve body 82. The bore diameter d is generally related to the diameter of an intended guide wire and may be in the range of approximately 0.03 to 0.2 inches. For relative comparison, the diameter of the valve body D may be in the range of approximately 0.4 to 0.8 inches. As shown in FIG. 12, the slot 83 may extend deeper than the bore 90 such that the bottom surface 91 is proximally spaced from the proximal surface of the bridge portion 84.

Optionally, a pilot hole 92 extends through the bridge portion 84 and exits out the body distal surface 94. The pilot hole 92 is preferably co-axial with the bore 90. The guide hole 92 has a minimal diameter, for example, about or smaller than the diameter of a guidewire, and serves to provide a propagation point to split the bridge portion 84 and allow passage of an instrument through the valve 80. In normal assembly as described below, the dilator 20 will be the first instrument passed through the valve 80. The dilator distal tip 37 will be guided to the pilot hole 92 by the conical surface 89 and the bore 90. As the distal tip 37 reaches the pilot hole 92, it will pierce the bridge portion 84, with the bridge portion 84 splitting outwardly from the pilot hole 92. As the dilator stem 20 passes, the resiliency of the valve 80 will cause the valve 80 to seal against the stem 20 as it extends therethrough. The valve 80 will function in a similar manner as a catheter or other instrument is passed through the valve 80. In each case, which ever instrument is passed through the valve 80, the bridge 84 will slit only enough to pass the particular device and will effectively create a custom passage sized just to the device passing through. As the dilator 20 or other instrument is removed, the resiliency of the valve 80 will cause the valve 80 to substantially seal upon itself.

Referring to FIGS. 9 and 12, the distal surface 94 of the valve body 82 includes a pair of opposed arcuate grooves 96. Each groove 96 extends slightly less than 180.degree. such that the grooves 96 are separated by opposed non-grooved portions 95 of the distal surface 94. The non-grooved portions 95 are preferably co-planar with the slot 83. The grooves 96 in conjunction with the non-grooved portions 95 provide a resilient hinge effect for the valve 80. As an instrument or the like is passed through the valve 80, the central portion of the valve body 82 will begin to deflect distally over an arcuate path as indicated by arrows A in FIG. 12. The grooves 96 provide space for the proximate portions 97 of the distal surface 94 to move during such deflection to allow easier passage, while the non-grooved portions 95 provide some rigidity and assist in restoring the valve central portion to it original position as the instrument is removed.

Referring to FIGS. 13-19, another exemplary valve 80' will be described. The valve 80' is similar to the prior embodiment and has a cylindrical body 82' with a diameter substantially equal to or slightly larger than the inside diameter of the hub body annular wall 58. While the valve body 82' is shown as cylindrical, it may have any other shape which complements the shape of the valve seat 60 and annular wall 58. The body 82' extends between a proximal surface 86' and a distal surface 94'. A bisecting slot 83' extends into the proximal surface 86' across the body 82' through the center thereof such that the body 82' includes opposed body halves 82a' and 82b'. The slot 83' terminates prior to the distal surface 94' such that the body halves 82a' and 82b' are joined by a bridging portion 84' along the distal surface 94'. The bridging portion 84' has a reduced thickness t1 and t2 relative to the total thickness T of the primary valve body 82', i.e. excluding the thickness of the convex portion 99'. In the present embodiment, the bridge portion 84' has varying thicknesses t1 and t2, with the central thickness t1 being larger than the thickness t2, however, the bridge portion 84' may have a constant thickness, for example, equal to t2. Preferably, the thickness t2 of the outer bridging portion is between approximately 0.003 to 0.012 inches and more preferably between approximately 0.005 to 0.009 inches. Preferably, the thickness t1 of the central bridging portion is between approximately 0.003 to 0.012 inches and more preferably is between approximately 0.005 to 0.009 inches. For relative comparison, the valve body thickness may be about 0.1 inches. With this configuration, the bridging portion 84' retains the body halves 82a', 82b' together prior to assembly and acts to seal the through passage 42.

In the present embodiment, the valve body 82' is preferably molded as a unitary component and the slot 83' is formed through a post molding process, for example, cutting, leaving just the bridge portion 84' extending between the halves 82a', 82b', however, the valve body 82' may be otherwise formed. For example, the body halves 82a', 82b' may be formed as separate components which are joined by the bridge portion 84' after formation or the halves 82a' and 82b' may be molded with a slot therebetween and just the bridge 84' extending therebetween. Preferably, the valve 80' is constructed of silicone, however, those skilled in the art will recognize that the valve 80' may be constructed out of any material that is sufficiently resilient to accommodate the objects inserted therethrough and return to a closed position. The material preferably has a durometer between 10 A to 40 A. In the presently illustrated embodiment wherein the slot 83' is created by post mold scoring, the width G of the slot 83' approaches zero as the material of the halves 82a', 82b' comes back together.

The proximal surface 86' defines an outer annular planar portion 87' that is substantially perpendicular to the longitudinal axis L when the valve is assembled within the sheath hub 50. An annular groove 88' is defined along the planar portion 87' and is configured to receive a retaining ridge 116 of the cap members 100 and also facilitates hinging of a center portion of the valve body 82' as an item is passed through the valve 80'. A plurality of alignment holes 98' extend from the distal surface 94' to the proximal surface 86' and are defined circumferentially spaced about the planar portion 87'. While the alignment holes 98' are illustrated extending completely through the body 82', such is not required. Alternatively, the alignment holes 98' may be formed as blind holes opening at the distal surface 94'.

The alignment holes 98' are configured to receive respective ones of the alignment posts 64 of the valve seat 60. In the present embodiment, the alignment holes 98' are illustrated in a symmetrical configuration about one of the axis of the valve, however, the alignment holes 98' may be positioned in a non-symmetrical configuration about all axis as in the previous embodiment. In either event, the alignment posts 64 are arranged in a corresponding configuration.

Figure 18:
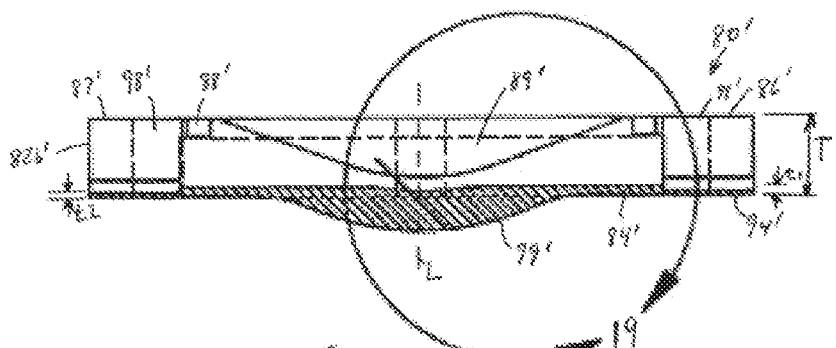
FIG. 18 is a cross-sectional view along the line 18-18 in FIG. 13.

Radially inward of the planar portion 87', the proximal surface 86' defines a conical, concave portion 89' extending distally. As seen in FIG. 18, the distal surface 94' defines a convex area 99' below the conical, concave portion 89'. The bridge 84' extends across the convex area 99'. The concave portion 89' on the proximal surface 86' and the convex area 99' on the distal surface 94' allow the two sealing faces of the body halves 82a' and 82b' to come back together as the dilator or other medical device is removed.

The present embodiment does not include a bore as in the previous embodiment, but instead includes a bisecting slit 150 that extends through the valve body 82' from the proximal surface 86' and out the distal surface 94'. The bisecting slit 150 is not co-planar with the slot 83' but instead is at an angle .OMEGA., see FIG. 15, relative to the slot 83'. The angle .OMEGA. is preferably in a range of approximately 45.degree. to 135.degree. and is most preferably equal to about 90.degree. In this manner, the sealing function of the slit 150 and the splitting function of the slot 83' are separated. While a single slit 150 is illustrated, multiple splits at different angles relative to the slot 83' may be provided.

Figure 19:
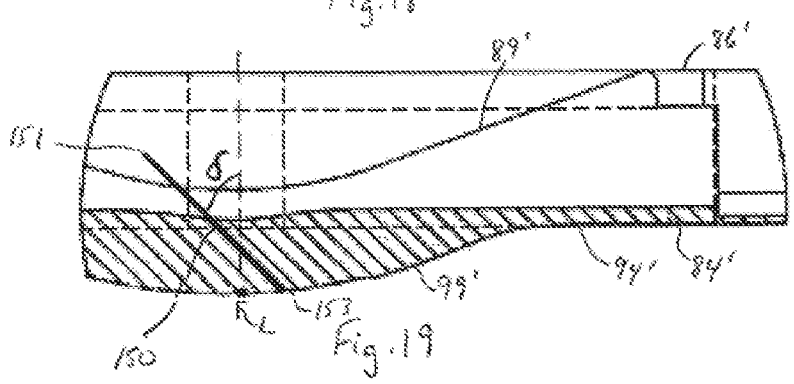
FIG. 19 is an expanded view of a portion of the valve of FIG. 18.
Figure 20:
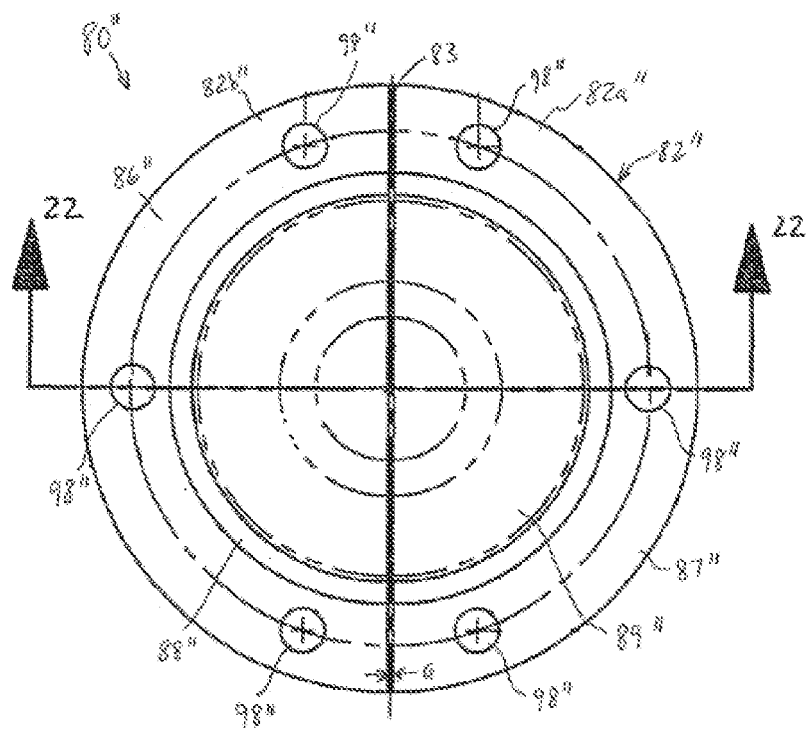
FIG. 20 is a top perspective view of another exemplary valve in accordance with an embodiment of the invention.
Figure 21:
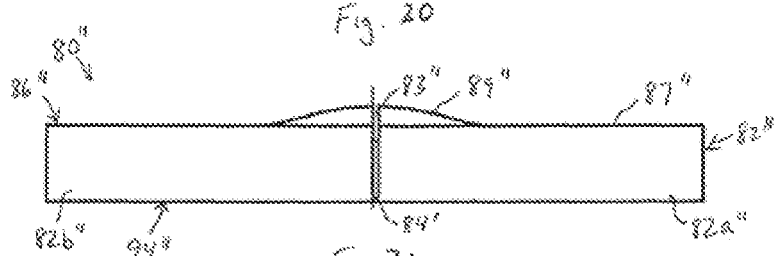
FIG. 21 is a side elevation view of the exemplary valve of FIG. 20.

Referring to FIGS. 18 and 19, it is preferable that the slit 150 is at an angle .delta. relative to the longitudinal axis L. The angle .delta. is preferably in a range of approximately 20.degree. to 70.degree. and is most preferably equal to about 45.degree. Preferably the slit 150 is positioned such that the proximal opening 151 of the slit 150 is on one side of the axis L while the distal exit 153 is on the opposite side of the axis L.

In normal assembly, the dilator 20 will be the first instrument passed through the valve 80'. The dilator distal tip 37 will enter the slit 150 and will thereby bypass the bridge portion 84', without necessitating splitting of the bridge portion 84. As the dilator stem 20 passes, the resiliency of the valve 80' will cause the valve 80' to seal against the stem 20 as it extends therethrough. The valve 80' will function in a similar manner as a catheter or other instrument is passed through the valve 80'. In each case, which ever instrument is passed through the valve 80', the slit 150 will open only enough to pass the particular device and will effectively create a general seal about the device passing through. As the dilator 20 or other instrument is removed, the resiliency of the valve 80' will cause the valve 80' to substantially seal upon itself, with the convex configuration of the conical portion 89' assisting in such sealing.

Referring to FIGS. 20-24, another exemplary valve 80" will be described. The valve 80" is similar to the prior embodiments and has a cylindrical body 82" with a diameter substantially equal to or slightly larger than the inside diameter of the hub body annular wall 58. While the valve body 82" is shown as cylindrical, it may have any other shape which complements the shape of the valve seat 60 and annular wall 58. The body 82" extends between a proximal surface 86" and a distal surface 94". A bisecting slot 83" extends into the proximal surface 86" across the body 82" through the center thereof such that the body 82" includes opposed body halves 82a" and 82b". The slot 83" terminates prior to the distal surface 94" such that the body halves 82a" and 82b" are joined by a bridging portion 84" along the distal surface 94". The bridging portion 84" has a reduced thickness t relative to the total thickness T of the valve body 82". Preferably, the thickness t of the bridging portion is between approximately 0.002 to 0.006 inches and more preferably between approximately 0.003 to 0.004 inches. For relative comparison, the valve body thickness may be about 0.1 inches. With this configuration, the bridging portion 84" retains the body halves 82a", 82b" together prior to assembly and acts to seal the through passage 42, but remains easily split as an instrument is passed through the valve 80" and easily separated when the sheath assembly 40 is split.

The valve body 82" is preferably molded as a unitary component with the bridge portion 84" extending between the halves 82a", 82b" and the slot 83" preformed, however, the valve body 82" may be otherwise formed. For example, the body halves 82a", 82b" may be formed as separate components which are joined by the bridge portion 84" after formation. Alternatively, the body 82" may be formed as a unitary structure and the slot is formed through a post molding process, for example, cutting, leaving just the bridge portion 84" extending between the halves 82a", 82b". Preferably, the valve 80" is constructed of silicone, however, those skilled in the art will recognize that the valve 80" may be constructed out of any material that is sufficiently resilient to accommodate the objects inserted therethrough and return to a closed position. The material preferably has a durometer between 10 A to 40 A. The width G of the slot 83" is preferably minimal and is generally dictated by the method of manufacture. In the present embodiment, the width G is preferably about 0.005 inches, however, the width G may approach zero, as explained above, or may be larger than 0.005 inches.

The proximal surface 86" defines an outer annular planar portion 87" that is substantially perpendicular to the longitudinal axis L when the valve is assembled within the sheath hub 50. An annular groove 88" is defined along the planar portion 87" and is configured to receive a retaining ridge 116 of the cap members 100 and also facilitates hinging of a center portion of the valve body 82" as an item is passed through the valve 80". A plurality of alignment holes 98" extend from the distal surface 94" to the proximal surface 86" are defined circumferentially spaced about the planar portion 87". While the alignment holes 98" are illustrated extending completely through the body 82", such is not required. Alternatively, the alignment holes 98" may be formed as blind holes opening at the distal surface 94".

The alignment holes 98" are configured to receive respective ones of the alignment posts 64 of the valve seat 60. In the present embodiment, the alignment holes 98" are illustrated in a symmetrical configuration about one of the axis of the valve, however, the alignment holes 98" may be positioned in a non-symmetrical configuration about all axis as in the previous embodiment. In either event, the alignment posts 64 are arranged in a corresponding configuration.

Figure 22:
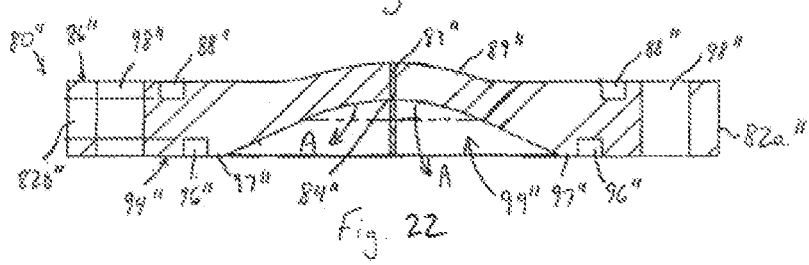
FIG. 22 is a cross-sectional view along the line 22-22 in FIG. 20.

Radially inward of the planar portion 87", the proximal surface 86" defines a conical, convex portion 89" extending proximally. As seen in FIG. 22, the distal surface 94" defines a concave area 99" below the conical, convex portion 89". The bridge 84" extends across the concave area 99". The convex portion 89" on the proximal surface 86" and the concave area 99" on the distal surface 94" allow the two sealing faces of the body halves 82a" and 82b" to come back together as the dilator or other medical device is removed.

The present embodiment does not include a bore as in the first embodiment, but optionally may include a pilot hole 92" co-axial with the valve body 82". In normal assembly, the dilator 20 will be the first instrument passed through the valve 80". The dilator distal tip 37 will enter the slot 83" and will pierce the bridge portion 84", with the bridge portion 84 splitting outwardly from the pilot hole 92". As the dilator stem 20 passes, the resiliency of the valve 80" will cause the valve 80" to seal against the stem 20 as it extends therethrough. The valve 80" will function in a similar manner as a catheter or other instrument is passed through the valve 80". In each case, which ever instrument is passed through the valve 80", the bridge 84" will slit only enough to pass the particular device and will effectively create a custom passage sized just to the device passing through. As the dilator 20 or other instrument is removed, the resiliency of the valve 80" will cause the valve 80" to substantially seal upon itself, with the concave configuration of the conical portion 89" assisting in such sealing.

Figure 23:
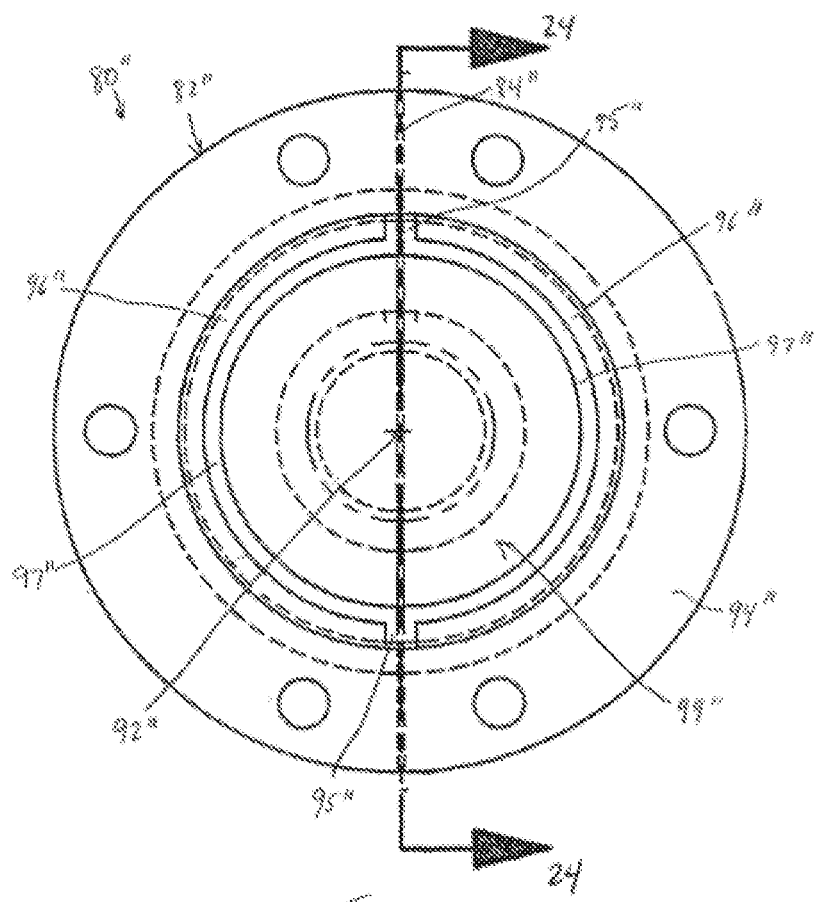
FIG. 23 is a bottom perspective view of the exemplary valve of FIG. 20.
Figure 24:
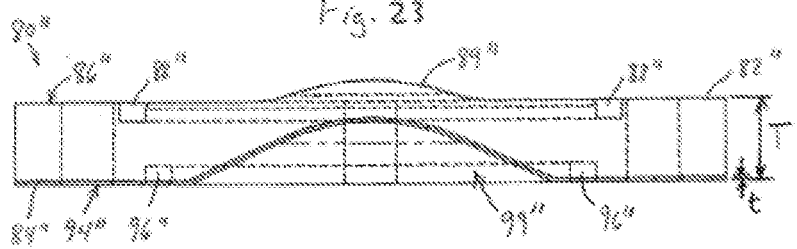
FIG. 24 is a cross-sectional view along the line 24-24 in FIG. 23.

Referring to FIGS. 22-24, the distal surface 94" of the valve body 82" includes a pair of opposed arcuate grooves 96". Each groove 96" extends slightly less than 180.degree. such that the grooves 96" are separated by opposed non-grooved portions 95" of the distal surface 94". The non-grooved portions 95" are preferably co-planar with the slot 83". The grooves 96" in conjunction with the non-grooved portions 95" provide a resilient hinge effect for the valve 80". As an instrument or the like is passed through the valve 80", the central portion of the valve body 82" will begin to deflect distally over an arcuate path as indicated by arrows A in FIG. 22. The grooves 96" provide space for the proximate portions 97" of the distal surface 94" to move during such deflection to allow easier passage, while the non-grooved portions 95" provide some rigidity and assist in restoring the valve central portion to its original position as the instrument is removed.

Figure 25:
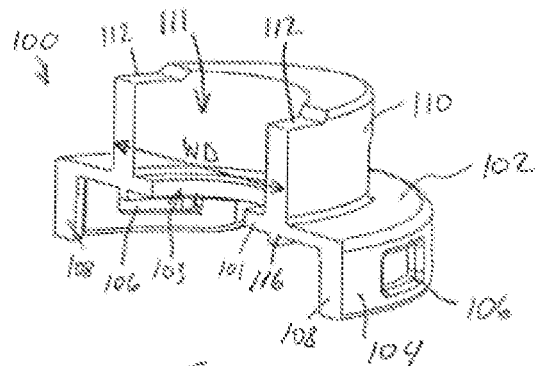
FIG. 25 is a front perspective view of an exemplary cap member in accordance with an embodiment of the invention.
Figure 26:
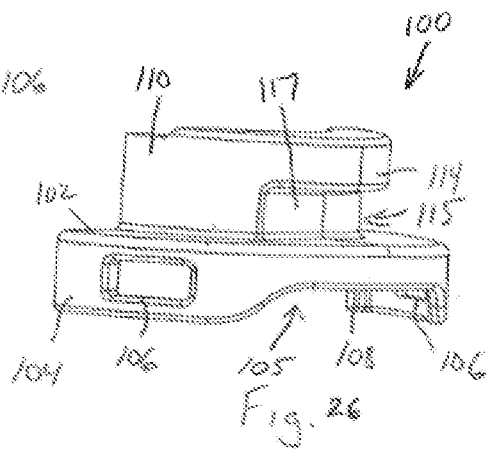
FIG. 26 is a rear perspective view of the exemplary cap member of FIG. 25.

Referring to FIGS. 25 and 26, an exemplary cap member 100 will be described. The sheath assembly 40 preferably uses two cap members 100 which are identical, however, paired cap members having different but complimentary configurations may be utilized. Each cap member 100 of the exemplary embodiment includes a semi-circular platform 102 with a depending semi-circular wall 104 along its outer circumference. The inside diameter of the wall 104 is approximately equal to or slightly larger than the outside diameter of the sheath hub wall 58. A pair of retaining openings 106 are defined through the circular wall 104, with each retaining opening 106 positioned and configured to receive and retain a respective retaining tab 57 of the sheath hub 50. While two openings 106 and two corresponding tabs 57 are described herein, more or fewer connections may be utilized. A portion of the wall 104 opposite the flat side 101 of the platform 102 defines a recess 105 which is configured to align with and receive a portion of a respective winged tab 70 when the cap member 100 is connected to the hub body 52. Each end of the semi-circular wall 104 has a returning wall portion 108 which extends radially inward and is configured to be received in a respective notch 54 of the hub body 52 when the cap member 100 is secured to the hub body 52. A semi-circular retaining ridge 116 depends from the distal surface of the platform 102 and is co-axial with the platform 102. The function of the ridge 116 will be described below.

A semi-circular opening 103 is defined through and co-axially with the platform 102 such that the open side of the opening 103 is along the flat side 101 of the platform. A proximally extending semi-circular wall 110 extends from the proximal side of the platform 102 about the opening 103, and defines an open passage 111. In the illustrated embodiment, the platform 101 extends radially inward of the wall 110 such that a diameter of the open passage 111 is slightly larger than the opening 103. However, the platform 101 may terminate at the wall 110 such that the open passage 111 and the opening 103 have substantially the same diameter. The outside surface of the wall 110 has a diameter WD. The diameter WD is approximately equal to or slightly smaller than the distance E between the engagement portions 34 of the dilator hub 22.

Figure 27:
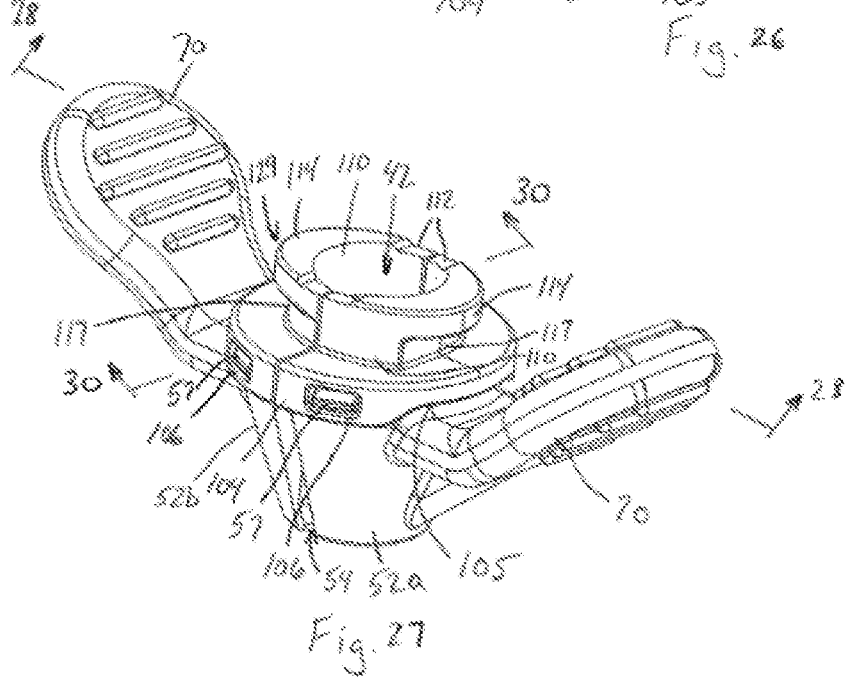
FIG. 27 is a perspective view of the exemplary hub assembly in an assembled condition with the sheath omitted.

As seen in FIGS. 27-29, when the cap members 100 are secured to the hub body 52 opposite one another, the two semi-circular openings 103 and the two semi-circular walls 110 define a substantially circular opening which forms a part of the through passage 42. The diameter of the opening 103 and the open passage 111 may be sized to correspond to a particular sheath or dilator size or a group of sizes within a given range. The ends of the wall 110 preferably have notches 112 on the proximal surface which when assembled define a stop receptacle 120 as will be described below.

The portion of the wall 110 opposite the flat side 101 of the platform 102 defines a radially outwardly extending proximal flange 114 which is longitudinally spaced from the platform 102 and extends beyond a longitudinal portion 117 of the wall 110 such that a receiving opening 115 is defined between the flange 114 and the platform 102. The distance from the flat side 101 of the platform 102 to the longitudinal portion 117 of the wall 110 is approximately one-half the diameter WD and the distance from the flat side 101 to the radial edge of the flange 114 is approximately one-half the distance F that the dilator hub extensions 33 are spaced. As such, when the cap members 100 are connected to the hub body 52, the wall 110 and portions 117 will define a diameter equal to WD which is approximately equal to or slightly smaller than the distance E between the engagement portions 34 of the dilator hub 22 and the flanges 114 will define a distance approximately equal to or slightly larger than the distance F that the dilator hub extensions 33 are spaced. The wall 110 and flanges 114 thereby define the locking portion 129 of the sheath assembly 40.

Having described the components of the sheath hub 50, assembly thereof will be described with reference to FIGS. 2 and 27-30. While assembly is described with reference to the valve 80, it is appreciated that the valve 80' may be utilized in the same manner. It is noted that the sheath body 44 is not illustrated in FIGS. 27-30, but typically the sheath body 44 will be attached to the hub body 52 prior to final assembly of the sheath hub 50. The valve 80 is positioned on the valve seat 60 within the hub body wall 58. As the valve 80 is positioned, the alignment posts 64 are received within the alignment openings 98 (see FIG. 30) and the sheath hub wall 58 radially compresses the valve body 82 such that the width of the slot 83 is reduced. As explained above, the posts 64 and openings 98 are arranged such that the valve 80 can only be properly positioned in the desired orientation, i.e. with the proximal surface 86 facing proximally and the slot 83 aligned with the space between the two cap members 100 and with the hub notches 54. With the valve 80 positioned on the seat 60, the distal surface 94 of the valve body 82 seats upon the seat planar surface 62. The distal surface 94 is spaced from the surface of groove 63. This space allows for compression of the valve body 82 when the cap members 100 are secured, thereby enhancing the seal between the distal surface 94 and the planar surface 62. The distal grooves 96 are positioned radially inward from the planar surface 62, aligned with the through passage 42, to facilitate hinging of the central portion of the valve body 82.

Once the valve 80 is positioned, each cap member 100 is connected to a respective valve body halve 52a, 52b. The cap member 100 is snapped onto the valve body 52, with respective retaining tabs 57 received in the retaining openings 106 as the wall 104 extends about the hub wall 58. The platforms 102 preferably slightly compress the valve body 82 when the cap members 100 are connected. Each cap member 100 is preferably separably connectable such that interconnection between the two cap members 100 is not required to maintain the cap members 100 in position. The cap members 100 are separated from one another by a slot which aligns with the notches 54. With the cap members 100 in place, the openings 103 and 111 are co-axial with the tapered portion 89 and bore 90 of the valve 80. The retaining ridges 116 are received in the corresponding grooves 88 on the proximal surface 86 of the valve body 82. The ridges 116 retain the out perimeter of the valve body 82 secure and enhance the seal on seat planar surface 62 while allowing the central portion of the valve body 82, radially inward of the grooves 88, to hingedly flex during insertion of an instrument. As shown in FIG. 29, the opposed notches 112 of adjacent cap members 100 define a stop receptacle 120.

With the sheath hub 50 assembled, the dilator 20 may be inserted therein and locked in place by engagement of the locking portions 39, 129 as described with reference to FIGS. 31-33. Referring to FIG. 31, the dilator stem 36 is passed through the opening 111 defined by the cap members 100 and then through the valve 80 (not shown in FIG. 31) and into the sheath body 44. During insertion, the dilator 20 is oriented such that the dilator hub platform 32 is transverse to the direction of the flanges 114 of the cap members 100. With this orientation, the dilator stem 36 may be fully inserted with the cap member walls 110 received between the engagement portions 34 of the dilator hub 22 as shown in FIG. 32. The engagement portions 34 contact the cap member platforms 102 upon full insertion.

After the dilator 20 has been fully inserted relative to the sheath assembly 40, the dilator hub 22 is rotated, as indicated by arrow B in FIG. 33, to the locking position. As the dilator hub 22 is rotated, the cap member flanges 114 are received in the locking grooves 45 of the dilator hub 22 and the engagement portions 34 are received in the receiving openings 115. The cap member wall portions 117 are each tapered at one end to facilitate passage of the engagement portions 34 into the receiving openings 115 while the opposite ends of the wall portions 117 define a stop 121 which prevent over rotation of the dilator hub 22 relative to the sheath hub 50. Rotation from the initial fully inserted position to the locked position illustrated in FIG. 33 is preferably over approximately 90.degree. As the dilator hub 22 reaches the locked position, the stop members 25 are received in the stop receptacle 120 such that a disengaging rotation force is necessary to unlock the dilator hub 22 relative to the sheath hub 50. Engagement of the locking portions 39 and 129 prevents longitudinal movement between the dilator 20 and the sheath assembly 40. The dilator and sheath assembly 10 is now ready for use as illustrated in FIG. 1.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

The invention claimed is:

1. A valve for sealing a hub of a tear-away sheath assembly, the valve comprising:
   a valve body having a proximal surface and a distal surface;
   a central portion of the proximal surface of the valve body which is concave and defines a concave proximal portion;
   a bisecting slot extending into and across the concave proximal portion of the proximal surface to form two opposed halves of the valve body;
   the bisecting slot extending a depth into the valve body, with the depth of the bisecting slot being less than a thickness of the valve body to provide a remaining portion of the valve body distally of the bisecting slot; and,
   a bridge defined by the remaining portion of the valve body and between the two opposed halves of the valve body and extending along the distal surface such that the two opposed halves of the valve body are joined by the bridge along the distal surface and wherein the bridge has a bridge thickness between 0.002 and 0.006 inches such that the bridge can be easily split into the two opposed halves as an instrument is passed through the valve.

2. The valve according to claim 1 wherein the valve body includes a groove in the distal surface extending about the central portion and a plurality of alignment holes extending from the distal surface to the proximal surface.

3. The valve according to claim 1 wherein a portion of the distal surface of the valve body opposite the concave proximal portion is convex.

4. The valve according to claim 1 wherein a sealing slit extends through the valve body from the proximal surface of the valve body to the distal surface of the valve body.

5. The valve according to claim 4 wherein the sealing slit extends at an angle between 45° to 135° relative to the bisecting slot.

6. The valve according to claim 5 wherein the sealing slit extends at an angle of approximately 90° relative to the bisecting slot.

7. The valve according to claim 4 wherein the sealing slit extends at an angle between 20° to 70° relative to a longitudinal axis of the valve body.

8. The valve according to claim 7 wherein the sealing slit extends at an angle of approximately 45° relative to the longitudinal axis of the valve body.

9. The valve according to claim 7 wherein a proximal opening of the sealing slit is on one side of the longitudinal axis and a distal exit of the sealing slit is on an opposite side of the longitudinal axis.

10. The valve according to claim 1 wherein the valve body includes a plurality of post receiving apertures extending into the distal surface of the valve body.

11. The valve according to claim 10 wherein the plurality of post receiving apertures are in a non-symmetrical pattern relative to at least one axis of the valve body.

12. The valve according to claim 10 wherein the plurality of post receiving apertures are in a non-symmetrical pattern relative to first and second axes of the valve body and are orthogonal to each other.

13. The valve of claim 1 wherein the bisecting slot extends more than half the thickness of the valve body.

14. A tear-away sheath assembly comprising:
an elongated hollow sheath body having a proximal body end, a distal body end, and a longitudinal axis extending between the proximal body end and the distal body end;
a sheath hub fixedly connected to the proximal body end, the sheath hub having a hub proximal end and a hub distal end and defining a through passage extending from the hub distal end to the hub proximal end and in communication with the hollow sheath body, the sheath hub further defining a valve seat in proximity to the hub proximal end;
a valve for sealing the hub of the sheath assembly, the valve comprising:
a valve body having a proximal surface and a distal surface;
a central portion of the proximal surface of the valve body which is concave and defines a concave proximal portion;
a bisecting slot extending into and across the concave proximal portion of the proximal surface to form two opposed halves of the valve body;
the bisecting slot extending a depth into the valve body, with the depth of the bisecting slot being less than a thickness of the valve body to provide a remaining portion of the valve body distally of the bisecting slot; and,
a bridge defined by the remaining portion of the valve body and between the two opposed halves of the valve body and extending along the distal surface such that the two opposed halves of the valve body are joined by the bridge and wherein the bridge has a bridge thickness between 0.002 and 0.006 inches such that the bridge can be easily split into the two opposed halves as an instrument is passed through the valve.

15. The tear-away sheath assembly of claim 14, wherein the sheath body includes at least one tear seam extending in a plane between the proximal body end and the distal body end and the sheath hub includes at least one longitudinal notch, and wherein the at least one tear seam, the at least one longitudinal notch and the bisecting slot are co-planar.

16. The tear-away sheath assembly of claim 14 further comprising one or more cap members defining a depending wall configured to receive a proximal portion of the sheath hub therein and wherein the wall and hub have interlocking tabs and recesses to secure the one or more cap members to the hub.

17. The tear-away sheath assembly of claim 14 wherein the valve includes a groove in the proximal surface of the valve body and one or more cap members with a portion of the one or more cap members being received in the groove.

18. A dilator and sheath assembly comprising:
a dilator including an elongated dilator stem having a proximal dilator end and a dilator hub fixedly connected to the proximal dilator end, wherein the dilator hub includes a locking portion at a distal portion thereof; and
an elongated hollow sheath body having a proximal body end, a distal body end, and a longitudinal axis extending between the proximal body end and the distal body end;
a sheath hub fixedly connected to the proximal body end, the sheath hub having a hub proximal end and a hub distal end and defining a through passage extending from the hub distal end to the hub proximal end and in communication with the hollow sheath body, the sheath hub further defining a valve seat in proximity to the hub proximal end;
a valve for sealing the hub of the sheath assembly, the valve comprising:
a valve body having a proximal surface and a distal surface;
a central portion of the proximal surface of the valve body which is concave and defines a concave proximal portion;
a bisecting slot extending into and across the concave proximal portion of the proximal surface to form two opposed halves of the valve body;
the bisecting slot extending a depth into the valve body, with the depth of the bisecting slot being less than a thickness of the valve body to provide a remaining portion of the valve body distally of the bisecting slot; and,
a bridge defined by the remaining portion of the valve body and between the two opposed halves of the valve body and extending along the distal surface such that the two opposed halves of the valve body are joined by the bridge and wherein the bridge has a bridge thickness between 0.002 and 0.006 inches;" is changed to "between 0.002 and 0.006 inches such that the bridge can be easily split into the two opposed halves as an instrument is passed through the valve;

wherein at least one cap member is configured to be secured to "the sheath hub", and comprises a mating locking portion such that the locking portion of the dilator hub and the mating locking portion of the at least one cap member provide a releasably locking engagement between the dilator and the sheath hub and wherein the mating locking portion of the at least one cap member comprises flanges and the locking portion of the dilator hub comprises corresponding locking grooves configured to receive the flanges.

19. The dilator and sheath assembly of claim 18 wherein the locking portion of the dilator hub and the mating locking portion of the at least one cap member are rotated over 90 degrees between the locking engagement and a non-locking engagement.

20. The dilator and sheath assembly of claim 19 wherein the locking portion of the dilator hub and the mating locking portion of the at least one cap member have a ramped engagement therebetween.

* * * * *